United States Patent [19]
Bankert et al.

[11] Patent Number: 6,041,789
[45] Date of Patent: Mar. 28, 2000

[54] CIGARETTE SUBSTITUTE DEVICE AND COMPOSITION FOR USE THEREIN

[75] Inventors: Timothy J. Bankert; Karen Dumais; Richard M. Maiorino, all of Tucson, Ariz.

[73] Assignee: K&B Technologies, L.L.C., Tucson, Ariz.

[21] Appl. No.: 09/239,165

[22] Filed: Jan. 28, 1999

[51] Int. Cl.$^7$ .................................................. A24F 47/00
[52] U.S. Cl. ........................................ 131/270; 131/273
[58] Field of Search ................................ 131/270, 273

[56] References Cited

U.S. PATENT DOCUMENTS

| | | | |
|---|---|---|---|
| 4,284,089 | 8/1981 | Ray | 131/270 |
| 4,774,971 | 10/1988 | Vieten | 131/273 |
| 4,793,366 | 12/1988 | Hill | 131/273 |
| 4,907,605 | 3/1990 | Ray et al. | 131/270 |
| 5,326,563 | 7/1994 | Spindler et al. | 131/270 |
| 5,501,236 | 3/1996 | Hill et al. | 131/270 |
| 5,666,979 | 9/1997 | Chase | 131/270 |
| 5,893,371 | 4/1999 | Rose et al. | 131/270 |

*Primary Examiner*—Christopher A. Fiorilla
*Attorney, Agent, or Firm*—Jerome M. Teplitz

[57] ABSTRACT

A non-pyrolytic cigarette substitute device which, in response to suction supplied by a user, delivers to the user a nicotine-simulating vapor mixture having a cigarette-like taste and aroma. The device has absorbed therein a solution of a volatile nicotinomimetic agonist in an amount effective for its released vapors to satisfy the physiological needs for nicotine of the user, and volatile palatability enhancing agents in amounts effective for their released vapors to neutralize any unpleasant taste and aroma of the nicotinomimetic agonist vapors and to impart a cigarette-like taste and aroma to the released vapor mixture.

21 Claims, 1 Drawing Sheet

CIGARETTE SUBSTITUTE DEVICE AND COMPOSITION FOR USE THEREIN

FIELD OF THE INVENTION

This invention relates to a cigarette substitute device for non-pyrolytic use and, more particularly, to such a device adapted to deliver to a user a nicotine-simulating vapor mixture having a cigarette-like taste and aroma.

BACKGROUND OF THE INVENTION

The health hazards associated with the smoking of combustible cigarettes, both to the smoker inhaling the smoke and to the non-smoker exposed to the second-hand smoke, have been well documented. For this reason, combustible cigarette smoking has increasingly become prohibited in many public places, such as restaurants, airplanes, airports, hospitals, shopping malls, the work place, etc., as well as socially unacceptable when a guest in a non-smoker's home. The social pressures to create a smoke-free society, while a boon to non-smokers, have made life rather unpleasant at times for habitual smokers finding themselves unable to satisfy their cigarette cravings.

There are several factors which are known to contribute to the habitual smoker's cigarette cravings. These include the psychological factors of holding the cigarette, placing it between the user's lips, puffing on it, and experiencing the taste and aroma of the smoke, as well as the physiological factor of nicotine dependency. Combustible cigarettes satisfy the physiological needs of the smoker by releasing as a component of the cigarette smoke vaporous nicotine, which is inhaled into the user's lungs, becomes rapidly assimilated into the bloodstream, and reaches the brain via arterial systems. After crossing the blood-brain barrier, the nicotine finally binds to the nicotinic or cholinergic receptors to release adrenergic transmitters, such as epinephrine, norepinephrine and dopamine, which are generally associated with pleasure and reward.

Because of the growing social unacceptability of combustible cigarette smoking, attempts have been made to provide cigarette substitute devices for non-pyrolytic use which simulate or closely approximate the look, feel and taste of combustible cigarettes and are capable of delivering nicotine vapor to the user through inhalation. Representative of those products are those described in the Ray U.S. Pat. No. 4,284,089, issued Aug. 18, 1981; the Hill U.S. Pat. No. 4,793,366, issued Dec. 27, 1988; and the Ray U.S. Pat. No. 4,813,437, issued Mar. 21, 1989. Such devices consist of an elongated tube having the approximate dimensions of an ordinary cigarette and housing a porous polymer plug serving as a reservoir for a source of vaporizable nicotine. The nicotine vapors are delivered to the user's lungs by the air drawn through the device by suction supplied by the user. These devices have failed to gain wide acceptance as a cigarette substitute, however, due to their inability to deliver sufficient and uniform amounts of nicotine to the user's lungs, an unpleasant taste, and an unsatisfactory shelf life. Most of these problems are due to the instability of the volatile liquid nicotine employed in these devices, which decomposes in the presence of oxygen and very rapidly dissipates from the system.

Thus, there is a continuing need for an adequate substitute for combustible cigarette smoking which will satisfy both the psychological and physiological needs of the habitual smoker without offending the senses of his non-smoking neighbor.

SUMMARY OF THE INVENTION

The present invention overcomes the deficiencies of the above-described prior art non-pyrolytic cigarette substitute devices, by providing a cigarette substitute device for non-pyrolytic use which, in response to suction supplied by a user, delivers to the user's lungs not nicotine vapors, but rather a nicotine-simulating vapor mixture having a cigarette-like taste and aroma. The cigarette substitute device of the present invention is similar in structure to the prior art non-pyrolytic cigarette substitute devices in comprising an elongated tube defining a passageway for air drawn through the device, and a porous polymeric material disposed within the tube. The inventive feature of the present invention is in the volatile liquid composition absorbed within the porous polymeric material. Instead of employing volatile liquid nicotine, the cigarette substitute device of the present invention employs a solution in a pharmaceutically acceptable liquid carrier medium of a volatile nicotinomimetic agonist in an amount effective for its released vapors to satisfy the physiological needs for nicotine of the user, and one or more volatile palatability enhancing agents in amounts effective for their released vapors to neutralize any unpleasant taste and aroma of the nicotinomimetic agonist vapors and to impart a cigarette-like taste and aroma to the released vapor mixture.

In its preferred embodiments, the novel volatile liquid composition used in the non-pyrolytic cigarette substitute device of the present invention comprises a solution in a pharmaceutically acceptable liquid carrier medium of:

(a) a volatile nicotinomimetic agonist in an amount within the range of from about 2 to about 25 percent by weight;

(b) nicotinic acid or a volatile derivative of nicotinic acid in an amount within the range of from about 3 to about 35 percent by weight; and (c) volatile tobacco flavoring in an amount within the range of from about 10 to about 90 percent by weight.

The above novel volatile liquid composition has been designated by the present inventors as "DEANATE™".

In the above composition, the nicotinomimetic agonist component is, by definition, a compound capable of mimicking the action of nicotine in binding to nicotinic or cholinergic receptors to release adrenergic transmitters such as epinephrine, norepinephrine and dopamine. Its released vapors thereby simulate the action of nicotine vapors and enable the cigarette substitute device of the present invention to satisfy the physiological needs for nicotine of the user without contributing to nicotine dependency. The nicotinic acid or derivative of nicotinic acid, and the tobacco flavoring components of the composition serve as palatability enhancing agents whose released vapors combine to provide the released vapor mixture with a cigarettelike taste and aroma and thereby enable the cigarette substitute device of the present invention to better satisfy the psychological needs of the user.

BRIEF DESCRIPTION OF THE DRAWINGS

A fuller understanding of the invention will become apparent from reading the following detailed description of the preferred embodiments along with the accompanying drawings in which.

DESCRIPTION OF THE PREFERRED EMBODIMENTS

Figure 1:
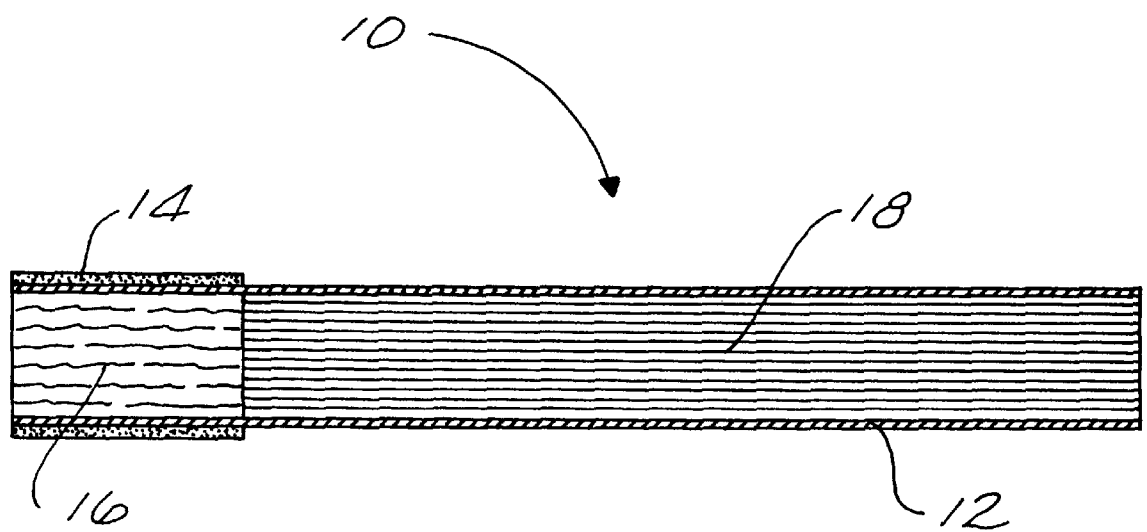
FIG. 1 is a side elevation in longitudinal section illustrating the preferred embodiment of the cigarette substitute device utilizing the features of the present invention.

Referring to FIG. 1 of the drawings, the cigarette substitute device 10 of the present invention includes a housing 12 in the form of an elongated tube which defines a passageway for air drawn though the cigarette substitute device. The housing 12 is preferably manufactured with a diameter, length and weight which approximate the size of a conventional combustible cigarette, and with the appropriate color to present the same appearance as a conventional combustible cigarette. In addition, a band 14 made of paper, cork or other suitable material may be applied around the mouthpiece 16 of the device 10 to simulate the appearance of the filter tip on a conventional cigarette. Alternatively, the mouth piece 16 may consist of an acetate or plastic filter end of conventional combustible cigarettes. Disposed within the housing 12 is a porous polymeric material 18, preferably in the form of polymeric fibers, and having absorbed therein the volatile liquid composition in accordance with the present invention.

The central component of the volatile liquid composition utilized in the non-pyrolytic cigarette substitute device of the present invention, is a volatile nicotinomimetic agonist whose released vapors simulate the action of nicotine vapors in binding to nicotinic or cholinergic receptors to release adrenergic transmitters such as epinephrine, norepinephrine and dopamine. The preferred nicotinomimetic agonists are selected from the group consisting of acetylcholine and biological precursors of acetylcholine, including ethanolamine (EA); N-methylethanolamine (MEA); N,N-dimethylethanolamine (DMEA); choline; salts of EA, such as hydrobromide, hydrochloride, hydroiodide, oleate; salts of MEA, such as hydrobromide, hydrochloride, hydroiodide, picrate; salts of DMEA, such as bitartrate, picrate, N-acetylglutamate, p-acetamidobenzoate, p-aminobenzoate; and salts of choline, such as ascorbate, bromide, chloride, iodide, bicarbonate, citrate, dihydrogen citrate, dehydrocholate, gluconate, salicylate, theophyllinate. Other nicotinomimetic agonists include epibatidine, anabasine, N-methylanabasine, levamisole and (S)-3-methyl-5-(1-methyl-2-pyrrolidinyl) isoxazole. In the most preferred embodiment of the volatile liquid composition of the present invention, the nicotinomimetic agonist component is DMEA. The nicotinomimetic agonist component is typically present in the composition in an amount within the range of from about 2 to about 25, preferably from about 10 to about 15, percent by weight.

The nicotinic acid or volatile derivative of nicotinic acid component of the composition serves as a palatability enhancing agent whose released vapors neutralize any unpleasant taste and aroma of the nicotinomimetic agonist vapors. This component is preferably ethyl nicotinate, but may also suitably be nicotinic acid (niacin); salts of nicotinic acid, such as sodium, picrate, ethanolamine, methylethanolamine, dimethylethanolamine, trimethylethanolamine; alkyl and benzyl esters of nicotinic acid; nicotinic acid hydrazide; nicotinamide; or nicotinamide ascorbate. This component is typically present in the composition in an amount within the range of from about 3 to about 35, preferably from about 15 to about 20, percent by weight.

The volatile tobacco flavoring component of the composition serves as an additional palatability enhancing agent whose released vapors impart a cigarette-like taste and aroma to the vapor mixture. This component may be either tobacco resinoid extract, synthetic tobacco flavoring, or a mixture of the two. Both tobacco resinoid extract and synthetic tobacco flavoring are commercially available, for example, from Bell Flavors and Fragrances, Inc. of Northbrook, Illinois. Tobacco resinoid extract, for example, is available as ethanolic extracts of various types of tobacco, such as Flue-cured, Fire-cured and Oriental tobacco. Synthetic tobacco flavoring is available in a number of different flavors, such as Flue-cured tobacco flavor, Burley tobacco flavor, Tobacco top flavor, Marlboro Lite tobacco flavor, Tobacco taste flavor, Tobacco flavor spicy, Full flavor impact, etc. Mixtures of different tobacco resinoid extracts and/or mixtures of different synthetic tobacco flavorings can suitably be used in formulating the volatile liquid composition utilized in the present invention. These components are typically present in the composition in a combined amount within the range of from about 10 to about 90, preferably from about 60 to about 75, percent by weight.

The liquid carrier medium used in the composition must be a pharmaceutically acceptable solvent, and will typically be an alcohol such as ethanol.

The pH of the volatile liquid composition of the present invention is preferably slightly basic, in the range of from about 7.5 to about 8.0. This pH insures that the nicotinomimetic agonist vapors released from the cigarette substitute device are in their base form rather than in their protonated form. This results in a greater rate of absorption of the vapors by the mucous membranes in the oral cavity.

Other flavoring agents, both natural and synthetic, may advantageously be added to the composition to suit the individual tastes of the user. This would include, for example, wintergreen, menthol, spearmint, peppermint, cinnamon, chocolate mint, banana, orange and lemon flavorings.

The polymeric material for absorbing the volatile liquid composition for use in the cigarette substitute device of the present invention, may be made from a variety of different polymers, such as polypropylene, polyethylene, polyvinyl chloride, polethylene-acrylic acid, cellulose acetate, and combinations thereof. The polymeric material may also take a wide variety of physical forms, such as fibers, flexible films, formed shapes or blocks, or rigid shapes. Preferably, the polymeric material is in the form of polymeric fibers. A particularly suitable polymeric fibrous material for use in the present invention comprises polypropylene microfibers bonded together into a self-supporting melt-blown web. The polypropylene meltblown web may advantageously be used in combination with cellulose acetate fibers.

The polymeric material may be loaded with the volatile liquid composition using any conventional technique for combining a liquid and an absorbent medium. This would include, for example, injecting the polymeric material with the liquid composition dipping the polymeric material into a bath of the liquid composition, or spraying or atomizing the liquid composition onto the polymeric material.

In a preferred formulation embodiment, the volatile liquid composition of the present invention comprises 12 percent by weight of N,N-dimethylethanolamine, 17 percent by weight of ethyl nicotinate, 63 percent by weight of ethanolic extract of tobacco resinoid, 5 percent by weight of synthetic tobacco flavoring, and the balance ethanol.

In the above formulation, all of the components are either food-grade compounds or harmless tobacco flavorings, none of which contribute to nicotine dependency. The nicotinomimetic agonist component of the formulation, N,N-dimethylethanolamine (DMEA), is an amino alcohol that is a natural product found in fish, especially sardines, herring and anchovies. Biochemically, DMEA is a CNS stimulant since it is methylated via normal metabolism to choline which is then utilized in the biosynthesis of acetylcholine, a brain neurotransmitter that is important for alertness, memory and learning, as well as for the biosynthesis of phospholipids that are necessary for cell membrane integrity such as lecithin. The ethyl nicotinate component of the formulation is biotransformed by enzymes that catalyze the de-esterification of ethyl nicotinate in the blood and liver into niacin (nicotinic acid) and ethanol. Niacin is a requirement for normal metabolism and also increases vascular dilation of capillaries which aids in cholesterol metabolism.

The above formulation may suitably be incorporated into and become absorbed by the porous polymeric material 18 within the housing 12 of the cigarette substitute device 10 illustrated in FIG. 1. When suction is applied to the mouthpiece 16 of the loaded device by a user, the formulation will release its vapor mixture into the air passing through the device in response to the applied suction. The vapor mixture will thereby be delivered to the user's lungs, and due to the nicotinomimetic agonist activity of the DMEA component, will simulate the action of nicotine in the user's body to satisfy the user's nicotine cravings without contributing to nicotine dependency. Futhermore, the released vapors of the formulation's other components will provide the vapor mixture with a cigarette-like taste and aroma to enhance the user's simulated smoking experience. Typically, the cigarette substitute device 10 will be loaded with sufficient formulation so as to satisfy the nicotine cravings of an average pack-a-day smoker for up to 10 to 12 hours of use, equivalent to approximately 12 to 15 conventional combustible cigarettes.

What is claimed is:

1. A cigarette substitute device for non-pyrolytic use, said device adapted to deliver to a user a nicotine-simulating vapor mixture having a taste and aroma similar to a cigarette in response to suction supplied by the user, said device comprising:
   (a) an elongated tube defining a passageway for air drawn through said device;
   (b) a porous polymeric material disposed within said tube; and
   (c) a volatile liquid composition absorbed within said polymeric material and adapted to release said vapor mixture into air drawn through said device in response to said suction, said composition comprising a solution in a pharmaceutically acceptable liquid carrier medium of:
      (i) a volatile nicotinomimetic agonist in an amount effective for its released vapors to satisfy physiological needs for nicotine of the user; and
      (ii) one or more volatile palatability enhancing agents in amounts effective for their released vapors to neutralize any unpleasant taste and aroma of the nicotinomimetic agonist vapors and to impart to the vapor mixture a taste and aroma similar to a cigarette.

2. The cigarette substitute device of claim 1, wherein said nicotinomimetic agonist is selected from the group consisting of acetylcholine and biological precursors of acetylcholine.

3. The cigarette substitute device of claim 2, wherein said nicotinomimetic agonist is a biological precursor of acetylcholine selected from the group consisting of ethanolaamine, N-methylethanolamine, N,N-dimethylethanolamine, choline, and salts thereof.

4. The cigarette substitute device of claim 3, wherein said nicotinomimetic agonist is N,N-dimethylethanolamine.

5. The cigarette substitute device of claim 1, wherein said volatile palatability enhancing agents are selected from the group consisting of nicotinic acid, derivatives of nicotinic acid, tobacco resinoid extracts, synthetic tobacco flavorings, and mixtures thereof.

6. The cigarette substitute device of claim 5, wherein said volatile palatability enhancing agents comprise a mixture of ethyl nicotinate and volatile tobacco flavoring.

7. The cigarette substitute device of claim 6, wherein said volatile tobacco flavoring comprises a mixture of tobacco resinoid extract and synthetic tobacco flavoring.

8. The cigarette substitute device of claim 7, wherein said nicotinomimetic agonist is N,N-dimethylethanolamine.

9. The cigarette substitute device of claim 1, wherein said composition has a pH in a range of from about 7.5 to about 8.0.

10. The cigarette substitute device of claim 1, wherein said polymeric material is in the form of polymeric fibers.

11. The cigarette substitute device of claim 10, wherein said polymeric fibers comprise polypropylene microfibers bonded together into a self-supporting melt-blown web.

12. The cigarette substitute device of claim 11, wherein said polymeric fibers further comprise cellulose acetate fibers.

13. The cigarette substitute device of claim 1, wherein said composition comprises said nicotinomimetic agonist in an amount within a range of from about 2 to about 25 percent by weight, nicotinic acid or a volatile derivative of nicotinic acid in an amount within a range of from about 3 to about 35 percent by weight, and volatile tobacco flavoring in an amount within a range of from about 10 to about 90 percent by weight.

14. The cigarette substitute device of claim 13, wherein said nicotinomimetic agonist is N,N-dimethylethanolamine, said nicotinic acid or volatile derivative of nicotinic acid is ethyl nicotinate, and said volatile tobacco flavoring is a mixture of tobacco resinoid extract and synthetic tobacco flavoring.

15. The cigarette substitute device of claim 14, wherein said composition comprises from about 10 to about 15 percent by weight of said N,N-dimethylethanolamine, from about 15 to about 20 percent by weight of said ethyl nicotinate, and from about 60 to about 75 percent by weight of said volatile tobacco flavoring.

16. A volatile liquid composition for use in a non-pyrolytic cigarette substitute device, said composition comprising a solution in a pharmaceutically acceptable liquid carrier medium of:
   (a) a volatile nicotinomimetic agonist in an amount within a range of from about 2 to about 25 percent by weight;
   (b) nicotinic acid or a volatile derivative of nicotinic acid in an amount within a range of from about 3 to about 35 percent by weight; and
   (c) volatile tobacco flavoring in an amount within a range of from about 10 to about 90 percent by weight.

17. The composition of claim 16, wherein said nicotinomimetic agonist is selected from the group consisting of acetylcholine and biological precursors of acetylcholine.

18. The composition of claim 17, wherein said nicotinomimetic agonist is a biological precursor of acetylcholine selected from the group consisting of ethanolamine, N-methylethanolamine, N,N-dimethylethanolamine, choline, and salts thereof.

19. The composition of claim 18, wherein said nicotinomimetic agonist is N,N-dimethylethanolamine, said nicotinic acid or volatile derivative of nicotinic acid is ethyl nicotinate, and said volatile tobacco flavoring is a mixture of tobacco resinoid extract and synthetic tobacco flavoring.

20. The composition of claim 19, wherein said composition comprises from about 10 to about 15 percent by weight of said N,N-dimethylethanolamine, from about 15 to about 20 percent by weight of said ethyl nicotinate, and from about 60 to about 75 percent by weight of said volatile tobacco flavoring.

21. The composition of claim 16, wherein said composition has a pH in a the range of from about 7.5 to about 8.0.

* * * * *